United States Patent [19]

Yoshida et al.

[11] Patent Number: 5,489,572
[45] Date of Patent: Feb. 6, 1996

[54] METHODS FOR REDUCING NITRATE NITROGEN AND OXALIC ACIDS CONTENTS NIN PLANTS

[75] Inventors: Ryuji Yoshida, Toyama; Tohru Tanaka; Yasushi Hotta, both of Saitama, all of Japan

[73] Assignees: Cosmo Research Institue; Cosmo Oil Co., Ltd., both of Tokyo, Japan

[21] Appl. No.: 292,024

[22] Filed: Aug. 18, 1994

[30] Foreign Application Priority Data

Aug. 19, 1993 [JP] Japan .................................. 5-205078
Aug. 19, 1993 [JP] Japan .................................. 5-205079

[51] Int. Cl.⁶ ........................................... A01N 37/44
[52] U.S. Cl. ............................................. 504/320
[58] Field of Search ................................... 504/320

[56] References Cited

U.S. PATENT DOCUMENTS 5,298,482  3/1994  Tanaka et al. ................... 504/320

OTHER PUBLICATIONS

Experientia, vol. 39, 1983, Basel/Switzerland, "Stimulation of nitrate reductase activity by delta amino levulinic acid in excised maize leaves," S. N. Mishra et al., pp. 1118–1120.

*Primary Examiner*—S. Mark Clardy
*Assistant Examiner*—Brian G. Bembenick
*Attorney, Agent, or Firm*—Sughrue, Mion, Zinn, Macpeak & Seas

[57] ABSTRACT

Methods for reducing nitrate nitrogen and oxalic acid contents in plants, each of which comprises applying 5-aminolevulinic acid, a salt thereof or a mixture thereof. Nitrate nitrogen and oxalic acid contents in plants having high nitrate nitrogen and oxalic acid contents can be reduced effectively and easily.

9 Claims, No Drawings

METHODS FOR REDUCING NITRATE NITROGEN AND OXALIC ACIDS CONTENTS NIN PLANTS

FIELD OF THE INVENTION

This invention relates to methods capable of reducing, when applied to plants, the content of nitrate nitrogen which causes the formation of toxic nitrosamine and the content of oxalic acid that spoils taste, nutrition and like qualities.

BACKGROUND OF THE INVENTION

It is known that nitrate nitrogen present in food is partly reduced into nitrous acid by enteric bacteria in the living body and the nitrous acid thus formed results in the formation of mutagenic nitrosamine through its binding with secondary amine present in other food. Nitrosamine is toxic for human health because it is considered to trigger the formation of cancers, tumors and the like. In consequence, great concern has been directed toward the reduction of nitrate nitrogen content in food.

In addition, since the incorporation of nitrate nitrogen into the human body originates from food, particularly from vegetables, it is most important to reduce the nitrate nitrogen content in vegetables.

On the other hand, the problems caused by nitrate nitrogen are common not only in human provisions but also in forage crops for domestic animals. Because of this, a standard nitrate nitrogen content in feed has been established, and reduction of the nitrate nitrogen level in feed therefore is an essential subject to be accomplished.

In view of the above, cultivation methods, especially fertilizer application methods, have been examined for the reduction of nitrate nitrogen content in plants. In these methods, the amount of fertilizer applied is reduced or a slow-acting fertilizer is used. However, such countermeasures limit the quantity and quality of fertilizers and therefore cause problems of slow growth and small yield of plants in comparison with commonly used cultivation methods.

Also, a method in which the nitrate nitrogen content in plants is reduced by the use of a fertilizer containing a nitrification inhibiting agent has been developed and partly put into practical use, but such a method resulted in high cost and its effect in reducing the nitrate nitrogen content was not sufficient.

Oxalic acid is an organic acid widely distributed in plants and takes part in the cause of the harsh taste of plants as a component of the "lye". In consequence, the oxalic acid content is one of the important factors which determine the quality of vegetables and the like. Especially, with the recently increasing occasion of eating vegetables raw in the form of salad and the like, great concern has been directed toward the reduction of the oxalic acid content in vegetables from the standpoint of taste.

On the other hand, when vegetables are considered from the dietetics point of view, oxalic acid is not desirable because of its nature to inhibit absorption of calcium into the living body by forming an insoluble material through its bonding with calcium. Also, oxalic acid causes calculus because it occupies more than 60% by weight of the urinary stone components.

In addition, since incorporation of oxalic acid into human body originates mostly from vegetables, it is important to reduce the oxalic acid content in vegetables.

In the conventional cooking of spinach, komatsuna (a kind of Chinese cabbage) and the like, their oxalic acid content is reduced by the so-called "removal of harsh taste" in which water is allowed to slop over in boiling them, but merely about 20% of the total amount of oxalic acid is reduced by such a means.

Though attempts have been made to produce vegetables with low oxalic acid content by selecting appropriate varieties and controlling fertilizer application, harvesting period and the like, satisfactory results have not been obtained yet. Also, very little actually is known about success in the development of a chemical agent which can reduce the oxalic acid content in vegetables.

SUMMARY OF THE INVENTION

In view of the above, it is therefore an object of the present invention to provide a method which can reduce the content of nitrate nitrogen and oxalic acid in plants.

Taking the aforementioned problems involved in the prior art into consideration, the inventors of the present invention have conducted intensive studies with the aim of finding a chemical agent which can reduce the content of nitrate nitrogen and oxalic acid in plants and found unexpectedly that 5-aminolevulinic acid, its salt or a mixture thereof functions to reduce the content of nitrate nitrogen and oxalic acid in plants to a satisfactory level. The present invention has been accomplished on the basis of this finding.

Accordingly, the present invention provides methods for reducing nitrate nitrogen content and oxalic acid content in plants each of which comprises applying 5-aminolevulinic acid, its salt or a mixture thereof.

Also, the present invention provides chemical agents for reducing nitrate nitrogen content and oxalic acid content in plants, each of which comprises 5-aminolevulinic acid, its salt or a mixture thereof.

In this connection, the present inventors already have proposed a method for applying 5-aminolevulinic acid or a salt thereof to plants by which growth, rooting, photosynthetic activity and the like of plants is promoted (U.S. Pat. No. 5,298,482). However, the effect of reducing the content of nitrate nitrogen and oxalic acid in plants as disclosed herein is a newly found effect which cannot be expected from the previously proposed growth-promoting and the like effects.

DETAILED DESCRIPTION OF THE PREFERRED EMBODIMENT

5-Aminolevulinic acid or a salt thereof to be used as the active ingredient of the present invention is a known natural compound which can be produced by any known method such as chemical synthesis, microbial production, enzymatic synthesis, extraction from natural sources or the like. In the case of the microbial production for example, the fermentation product may be used as it is without employing separation and purification steps, provided that the product does not contain substances which spoil the effect of the present invention. Examples of the salt of 5-aminolevulinic acid include acid addition salts such as the hydrochloride, phosphate, nitrate, sulfate, acetate, propionate, butyrate, valerate, citrate, fumarate, maleate, malate and the like salts and metal salts such as the sodium, potassium, calcium and the like salts.

In order to effect a reduction in the content of nitrate nitrogen and oxalic acid in plants by the method of the present invention, any treating method such as foliar application, soil treatment or the like may be used, provided that 5-aminolevulinic acid or a salt thereof is absorbed by plants. Any treating or application method can be used as long as the method produces the plant with the ability to absorb the 5-aminolevulinic acid or salt thereof. In the case of hydroponics and the like, 5-aminolevulinic acid may be used in the form of an aqueous solution to achieve root absorption.

When the method of the present invention is used in foliar application, it can contain preferably from 1 to 1,000 ppm, more preferably from 5 to 500 ppm, of 5-aminolevulinic acid, and it can be applied in an amount of preferably from 10 to 3,000 l, more preferably from 20 to 1,000 l, per 1,000 $m^2$. When the method of the present invention is applied to a plant whose leaves can hardly retain the active ingredient, it is preferable to use a spreader together with 5-aminolevulinic acid. The type and amount of the spreader are not particularly limited and can be determined appropriately in a conventional manner.

When the method of the present invention is used in soil treatment, it can be applied to soil in an amount of preferably from 0.5 to 800 g, more preferably from 1 to 300 g, of 5-aminolevulinic acid per 1,000 $m^2$.

When the method of the present invention is to be absorbed through roots of plants in the form of an aqueous solution such as the case of hydroponics, it contains preferably from 0.001 to 50 ppm, more preferably from 0.01 to 20 ppm, of 5-aminolevulinic acid.

5-Aminolevulinic acid exerts its effect satisfactorily by a single operation of any application process described above, but the effect is improved further by repeating the process several times. Though not particularly limited, the application may be carried out preferably at an early stage of plant growth.

5-Aminolevulinic acid may be used in the form of a mixture with other agricultural chemicals, fertilizers and the like, provided that they do not adversely affect of the present invention.

With regard to a method for reducing the nitrate nitrogen content in plants, as one of the methods of the present invention, plants to be treated with this method are not particularly limited, but its effect is markedly evident when a plant having a high nitrate nitrogen content, preferably 0.5% by weight or more, more preferably 1% by weight or more, of nitrate nitrogen of the total nitrogen content in the plant, is treated. Illustrative examples of such plants include vegetables such as spinach, Chinese cabbage, cabbage, lettuce and the like, pasture grasses such as maize, clover and the like and weeds such as a broad-leaved plantain, a Japanese knotweed, a wood sorrel, a sorrel and the like.

With regard to a method for reducing the oxalic acid content in plants, as another one of the methods of the present invention, plants to be treated with this method are not particularly limited, but its effect becomes markedly evident when a plant having a high oxalic acid content, preferably 50 mg or more of oxalic acid per 100 g of the plant, more preferably 100 to 5,000 mg of oxalic acid per 100 g of the plant, is treated. Illustrative examples of such plants include vegetables such as spinach, komatsuna (a kind of Chinese cabbage), garland chrysanthemum, sunny lettuce, celery, salad and the like, pasture grasses such as maize, clover and the like and weeds such as a broad-leaved plantain, a Japanese knotweed, a wood sorrel, a sorrel and the like.

The following examples are provided to further illustrate the present invention. It is to be understood, however, that the examples are given for purpose of illustration only and are not construed as limiting the scope of the present invention. Unless otherwise indicated herein, all parts, percents, ratios and the like are by weight.

EXAMPLE 1

On October 20, 11 spinach seeds (Glory, available from Takii Shubyo K.K.) were sowed in a pot of 1/500,000 $m^2$ filled with field soil.

As a basal fertilizer, 1.5 g of a compound fertilizer Sosai No. 3 ($N:P_2O_5:K_2O=15:15:15$) was applied to each pot but with no additional dressing.

As the seedlings grew under usual tending conditions in a greenhouse, thinning was repeated to select 3 uniform seedlings to be grown further in each pot.

On November 11, foliage treatment was carried out with 20 ml per pot of an aqueous solution containing 0, 50, 100 or 300 ppm of 5-aminolevulinic acid hydrochloride (hereinafter referred to as "5-ALA") and 0.1 ml/100 ml of a spreader (Approach (mainly composed of 50% of polyoxyethylenehexytane fatty ester and 20–30% of isopropyl alcohol), manufactured by Kao Corp.). Each treatment was carried out using 6 pots.

After further tending under usual conditions in the greenhouse, the plants were harvested on January 18 to measure the oxalic acid content in the leaves using a high performance liquid chromatography (HPLC) in a conventional manner.

The results obtained are shown in Table 1 below.

TABLE 1

| 5-ALA Conc. (ppm) | Total Oxalic Acid (mg/100 g FW*) |
| --- | --- |
| 0 | 665.0 |
| 50 | 335.0 |
| 100 | 420.0 |
| 300 | 335.0 |

*: flesh weight

As is evident from the results shown in Table 1 above, the oxalic acid content is greatly reduced by the treatment of the foliage with the agent of the present invention.

The thus harvested spinach plants were washed with water and subjected to sampling without cooking to examine "harsh taste". The results obtained are shown in Table 2 below. In this case, the panelists were not given any information about the spinach oxalic acid content, 5-ALA concentration and the like.

TABLE 2

| 5-ALA Conc. (ppm) | Panelists | | |
| --- | --- | --- | --- |
|  | A | B | C |
| 0 | ⊙ | o | o |
| 50 | o | Δ | X |
| 100 | o | Δ | X |
| 300 | o | Δ | X |

⊙: very strong in "harsh taste"
o: strong in "harsh taste"
Δ: weak in "harsh taste"
X: negligible in "harsh taste"

As is evident from the results shown in Table 2 above, "harsh taste" at the time of eating the uncooked vegetable is reduced by the method of the present invention, thus confirming the effect of the agent to reduce the so-called "lye".

EXAMPLE 2

Spinach plants (Glory, a western variety; available from Takii Shubyo K.K.) which had been cultivated and treated in the same manner as described in Example 1 were subjected to sampling to evaluate their "harsh taste". Panelists participated in this test were first- to third-year students at an elementary school who dislike spinach. The results are shown in Table 3 below. In this case, the panelists were not given any information about the spinach oxalic acid content, 5-ALA concentration and the like.

TABLE 3

| 5-ALA Conc. | Panelists | | | |
|---|---|---|---|---|
| (ppm) | A | B | C | D |
| 0 | o | o | o | o |
| 50 | o | Δ | Δ | o |
| 100 | o | Δ | X | Δ |
| 300 | Δ | Δ | X | X | o: too bitter to eat
Δ: bearable to eat
X: delicious

As is evident from the results shown in Table 3 above, the taste of the western spinach inherently having high oxalic acid content is improved by the method of the present invention to such a level that even children who dislike spinach can eat it.

EXAMPLE 3

On October 20, 11 komatsuna seeds (Osome, available from Takii Shubyo K.K.) were sowed in a pot of 1/500,000 m² filled with field soil.

As a basal fertilizer, 2.5 g of a compound fertilizer Yasai No. 3 ($N:P_2O_5:K_2O=15:15:15$) was applied to each pot but with no additional dressing.

As the seedlings grew under usual tending conditions in a greenhouse, thinning was repeated to select 3 uniform seedlings to be grown further in each pot.

On November 11, foliage treatment was carried out with 10 ml per pot of an aqueous solution containing 0, 50, 100 or 300 ppm of 5-ALA and 0.1 ml/100 ml of a spreader (Approach, manufactured by Kao Corp.). Each treatment was carried out using 6 pots.

After further tending under usual conditions in the greenhouse, the plants were harvested on January 18 to measure the oxalic acid content in leaves using HPLC in a conventional manner.

The results obtained are shown in Table 4 below.

TABLE 4

| 5-ALA Conc. (ppm) | Total Oxalic Acid (mg/100 g FW) |
|---|---|
| 0 | 185.0 |
| 50 | 85.0 |
| 100 | 92.0 |
| 300 | 78.0 |

As is evident from the results shown in Table 4 above, the oxalic acid content in komatsuna is reduced to half or more by its treatment with the agent of the present invention.

EXAMPLE 4

Seeding, cultivation and harvesting were carried out in the same manner as described in Example 1 and the nitrate nitrogen content in the plant leaves was measured using HPLC in a conventional manner to calculate the ratio of the nitrate nitrogen in total nitrogen. The results are shown in Table 5 below.

TABLE 5

| 5-ALA Conc. (ppm) | Nitrate Nitrogen Content (mg/100 g DW*) | Ratio** (%) |
|---|---|---|
| 0 | 4.83 | 14.59 |
| 50 | 5.00 | 9.06 |
| 100 | 4.20 | 6.71 |
| 300 | 3.57 | 6.41 |

*: dry weight
**: weight % of nitrate nitrogen in the total nitrogen

As is evident from the results shown in Table 5 above, the nitrate nitrogen content is reduced by the method of the present invention, with especially great reduction in the ratio of nitrate nitrogen to total nitrogen.

EXAMPLE 5

On June 11, 5 maize seeds (Yukijirushi Snowdent RM120, available from Yukijirushi K.K.) were sowed in a pot of 1/500,000 m² filled with field soil.

As basal fertilizers, 6 g of a compound fertilizer ($N:P_2O_5:K_2O=10:10:10$) and 5 g of Magporon (mainly composed of dolomite ($CaCO_3 \cdot MgCO_3$)) were applied to each pot but with no additional dressing.

As the seedlings grew under usual tending conditions in a greenhouse, thinning was repeated to select 2 uniform seedlings to be grown further in each pot.

On August 1, foliage treatment was carried out with 20 ml per pot of an aqueous solution containing 0, 50, 100 or 300 ppm of 5-ALA and 0.1 ml/100 ml of a spreader (Approach, manufactured by Kao Corp.). Each treatment was carried out using 6 pots.

After further tending under usual conditions in the greenhouse, the plants were harvested on August 14, air-dried and then pulverized to measure the nitrate nitrogen content using HPLC in a conventional manner and to calculate the ratio of nitrate nitrogen in the total nitrogen.

The results obtained are shown in Table 6 below.

TABLE 6

| 5-ALA Conc. (ppm) | Nitrate Nitrogen Content (mg/100 g DW*) | Ratio** (%) |
|---|---|---|
| 0 | 3.20 | 14.18 |
| 50 | 2.35 | 7.75 |
| 100 | 1.60 | 6.66 |
| 300 | 3.25 | 8.41 |

*: dry weight
**: weight % of nitrate nitrogen in the total nitrogen

As is evident from the results shown in Table 6 above, the nitrate nitrogen content is reduced by the method of the present invention, with especially great reduction in the ratio of nitrate nitrogen to total nitrogen.

While the invention has been described in detail and with reference to specific embodiments thereof, it will be apparent to one skill in the art that various changes and modifications can be made therein without departing from the spirit and scope thereof.

What is claimed is:

1. A method for reducing nitrate nitrogen content in a plant, which comprises applying 5-aminolevulinic acid, a salt thereof or a mixture thereof, wherein the nitrate nitrogen content in a plant to be treated is 0.5% or more by weight of the total nitrogen in said plant.

2. A method for reducing oxalic acid content in a plant, which comprises applying 5-aminolevulinic acid, a salt thereof or a mixture thereof, wherein a plant to be treated has an oxalic acid content of 50 mg/100 g of said plant or more.

3. The method according to claim 1 or 2, wherein said salt of 5-aminolevulinic acid is at least one salt selected from the group consisting of the hydrochloride, phosphate, nitrate, sulfate, acetate, propionate, butyrate, valerate, citrate, fumarate, maleate, malate, sodium, potassium and calcium salts.

4. The method according to claim 1 or 2, wherein a spreader is further present.

5. The method according to claim 1, which comprises treating foliage of said plant with 1 to 1,000 ppm of 5-aminolevulinic acid, a salt thereof or a mixture thereof.

6. The method according to claim 1, which comprises treating foliage of said plant with 1 to 1,000 ppm of 5-aminolevulinic acid, a salt thereof or a mixture thereof.

7. The method according to claim 5 or 6, wherein said plant is treated with 10 to 3,000 l per 1,000 $m^2$ of said compound.

8. The method according to claim 1 or 2, which comprises applying 5-aminolevulinic acid, a salt thereof or a mixture thereof to soil in which the plant is grown in an amount of 0.5 to 800 g/1,000 $m^2$.

9. The method according to claim 1 or 2, которые comprises hydroponically culturing said plant using a culture solution containing 0.001 to 50 ppm of 5-aminolevulinic acid, a salt thereof or a mixture thereof.

\* \* \* \* \*